United States Patent [19]

Nickell

[11] 3,992,187

[45] Nov. 16, 1976

[54] AMINOPENICILLANIC ACID OR PENICILLAMINE AS RIPENER FOR SUGARCANE

[75] Inventor: Louis G. Nickell, Honolulu, Hawaii

[73] Assignee: Hawaiian Sugar Planters', Honolulu, Hawaii

[22] Filed: Feb. 25, 1975

[21] Appl. No.: 552,921

Related U.S. Application Data

[63] Continuation-in-part of Ser. No. 455,955, March 28, 1974, Pat. No. 3,897,239.

[52] U.S. Cl. .......................................... 71/90; 71/96; 71/98; 71/103; 71/115
[51] Int. Cl.² ............................................ A01N 9/12
[58] Field of Search ................ 71/90, 98; 260/239.1

[56] References Cited

UNITED STATES PATENTS 2,749,230  6/1956  Kaplan .................................... 71/90
3,159,617  12/1964  Sheehan ........................... 260/239.1
3,505,056  4/1970  Nickell et al. .......................... 71/88

OTHER PUBLICATIONS

Crooks, "The Chemistry of Penicillin", (1949) Princeton Univ. Press, pp. 455–472.

Primary Examiner—Glennon H. Hollrah
Attorney, Agent, or Firm—Burns, Doane, Swecker & Mathis

[57] ABSTRACT

Sucrose yield of sugarcane is increased by treating the cane crop a few weeks prior to harvest with a ripening agent comprising 6-aminopenicillanic acid, D-penicillamine or DL-penicillamine, or derivatives or mixtures thereof.

11 Claims, No Drawings

AMINOPENICILLANIC ACID OR PENICILLAMINE AS RIPENER FOR SUGARCANE

CROSS-REFERENCE TO PARENT CASE

This application is a continuation-in-part of application Ser. No. 455,955, filed March 28, 1974, now U.S. Pat. No. 3,897,239.

FIELD OF THE INVENTION

This invention relates to an improvement in the production of sugar from sugarcane. More particularly it relates to a process for increasing the sugar yield of sugarcane by the application of certain penicillin precursors or derivatives to the maturing sugarcane plants in the field a few weeks prior to harvest, and it also relates to compositions of matter useful for this purpose.

THE PRIOR ART

As more fully described in parent application Ser. No. 455,955, the disclosure of which is hereby incorporated by reference, a number of chemical ripeners for sugarcane has been previously proposed. Some of these are disclosed, for example, in U.S. Patents Nos. 3,224,865; 3,245,775; 3,291,592; 3,482,959; 3,482,961; 3,493,361; 3,505,056; 3,660,072 and 3,671,219. Still other chemical agents which have been found successful or shown promise as sugarcane ripeners, such as cyclo-leucine, anisomycin and cycloheximide, are disclosed, for instance, in Hawaiian Planters' Record, Vol. 58, No. 5, pp. 71–79 (1970). The use of bacitracin is disclosed and claimed in copending application Ser. No. 455,954, filed Mar. 28, 1974, now U.S. Pat. No. 3,897,240, and the use of various specific penicillins and penicillin type compounds broadly is disclosed and claimed in the above-identified parent U.S. Pat. No. 3,897,239.

As previously stated, the more active ripeners differ widely from each other in terms of chemical structure as well as chemical and biological properties. In the search for effective ripeners failures continue to outnumber successes by a wide margin, and as of this date there is still no known screening test for determining the ripening activity of a compound other than to test it on maturing sugarcane. Moreover, because of toxicological or ecological concerns and the consequent possibility that rotation of use of different chemical ripeners in consecutive seasons in a given area may be preferable to the continued use of a single ripener or ripener mixture, the search for new sugarcane ripeners continues unabated.

OBJECTS OF THE INVENTION

It is an object of this invention to provide new and economically useful chemical ripening agents for sugarcane. A more general object is to increase the sucrose yield of sugarcane by chemically treating it during its maturation prior to harvest without introducing objectionable toxicological hazards. More specifically, it is an object of this invention to increase the sucrose yield of maturing sugarcane by treating a cane crop nearing its normal harvest time with a relatively inexpensive penicillin precursor or derivative which is sufficiently stable to provide the desired effect over a period of several weeks between application and a variable harvest date, but yet has a relatively low degree of persistence and is susceptible to autodecomposition or to decomposition by soil bacteria. A compound which increases the sucrose content only temporarily over a period of three weeks or less after application and then results in a substantial decrease is usually not a desirable chemical ripener except in situations where harvesting time can be rigidly programmed in advance in relation to the time of application of the chemical ripener.

SUMMARY OF THE INVENTION

According to the present invention the desired objectives have been achieved by the application of ripening compositions comprising 6-aminopenicillanic acid or a salt thereof, D-penicillamine or DL-penicillamine, or salts or sulfides thereof, or mixtures of two or more of the foregoing. More specifically, an excellent increase in sucrose yield has been obtained by applying a spray or dust comprising one or more of such compounds to maturing sugarcane stalks in a crop near the end of its normal maturation cycle, and harvesting such a crop some weeks later. The composition is applied directly to the stalks by spraying, dusting or the like in order that it be deposited on the stalks including the younger, growing parts thereof. The normal maturation cycle of sugarcane under conditions such as those prevailing in Hawaii is from about 18 to about 36 months, though in some areas sugarcane is ripe and ready for harvest in 9 to 12 months.

The preferred usage form is a mixture containing the penicillin compound in an aqueous solution or suspension utilizing one or a combination of known surface active agents commonly and variously used in the prior art as wetting agents, detergents or emulsifying agents. However, dry dusting compositions containing the penicillin compound and a solid diluent such as clay are also useful.

6-aminopenicillanic acid (6-APA) is a well known compound which is antibiotically inactive but is commonly used as an intermediate in the manufacture of synthetic penicillins which are active antibiotics. See U.S. Pat. No. 3,159,617. 6-APA forms water soluble salts with bases such as sodium, potassium or ammonium hydroxide; it forms sparingly soluble salts with organic bases such as benzathine or procaine; and it forms essentially insoluble salts with bases such as calcium or aluminum hydroxide. Both the free acid and its salts are useful in the present invention.

Other penicillin-type compounds which, though not active antibiotics, are useful in the present invention are the several forms of penicillamine, e.g., D-penicillamine, L-penicillamine, DL-penicillamine and their various salts such as their hydrochlorides, sulfates or phosphates. Various methods for synthesizing penicillamine are known and some are described, for instance, by Crooks in The Chemistry of Penicillin, Princeton University Press (1949), pp. 455–472. Useful sulfide derivatives of penicillamine include penicillamine disulfide, penicillamine cysteine disulfide and the like.

Penicillamine has the formula:

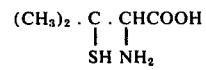

Penicillamine disulfide has the formula:

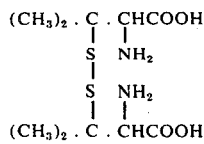

Penicillamine Cysteine disulfide has the formula:

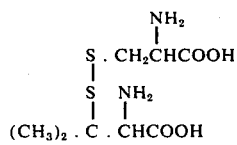

The possibility of using antibiotics, penicillin salts among them, as food supplements and growth stimulants for radishes, oats, grass and plants in general, has been previously suggested. See, for instance, Nickell, "Stimulation of Plant Growth by Antibiotics," Proceedings of the Society for Experimental Biology and Medicine, 80, 615–617 (1952); Nickell, "Antibiotics in the Growth of Plants," Antibiotics and Chemotherapy, 3, 449–459 (1953); Nickell et al, "Antibiotics and the Effects on Plant Growth," Journal of Agricultural and Food Chemistry, 2, 178–182 (1954); British Pat. No. (Nickell) 757,498; and U.S. Pat. No. 2,749,230. More particularly, for instance, it has been suggested that application of antibiotics such as water insoluble penicillin salts as fertilizer components or as additives in irrigation water will benefit vegetation by increasing the size or vigor of plants within a given period or will shorten the time required by the plants to reach normal maturity. However, the application of any penicillin compound directly to the maturing stalks of sugarcane or to any similar plants for the purpose of increasing the resulting sugar yield or for any other purpose, has not been previously suggested except in this applicant's own parent U.S. Pat. No. 3,897,239, referred to above.

The present discovery of the effective ripening activity of 6-APA and the penicillamine compounds is astonishing, as most antibiotically active compounds heretofore tested as potential sugarcane ripeners have been found to produce no useful effect in terms of a measurable or commercially measurable increase in the crop treated, and the usefulness of compounds which are not antibiotically active has been found to be equally unpredictable in this field.

In accordance with this invention, a sugarcane crop which is nearing the normal maturity stage, e.g., a crop in Hawaii which is 18 to 36 months of age, is treated with 6-APA or a penicillamine or with a composition containing one or more of such antibiotically inactive compounds about two to ten weeks before harvest, the preferred time for treatment being between about four and ten weeks prior to harvest.

Good results are obtained when the sugarcane crop is treated in the field at a rate in the range of from 1 to 4 pounds per acre of 6-APA or penicillamine or equivalent salt or derivative. However, higher rates (e.g., up to about 30 pounds of the chemical ripener or more per acre) or rates lower than 1 pound per acre can also be used. The optimum amount will vary somewhat depending on the particular mode of application, environmental conditions, time or year, and age and variety of cane being treated, but can be readily determined for each particular case by preliminary testing.

The active agent is conveniently applied in the field in the form of an aqueous solution, emulsion or suspension, i.e., in a liquid composition which may be sprayed onto the maturing cane plants from a boom-spray, or it can be dusted on from an airplane or the like as a dust composition which contains the active compound diluted with an inert solid such as clay.

In preparing suitable liquid compositions, surface active agents of the type described, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethyleneoxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the active ripener to the sugacane field in the form of an aqueous solution, suspension or emulsion having a concentration of active agent such that the application at the rate of from 5 to 20 gallons of liquid composition per acre will provide the required dosage of active chemical. However, the use of lower or higher gallonages may be preferred when a different dispensing mechanism is used.

The preferred carrier for the active ripening agent is water to which about 0.1 to 2% by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the ripening agents of the present invention constitute essentially the sole active ingredients in the treating composition, but they may also be applied in combination with other agents.

DESCRIPTION OF SPECIFIC EMBODIMENTS

EXAMPLE 1

Part A — Preparation of Treating Composition

A treating composition is prepared by weighing out 1 gram of 6-aminopenicillanic acid (6-APA) and dissolving it in approximately 6 ml of water. This solution is diluted with water to exactly 8 ml, 1 drop of commercial Tergitol NPX (liquid) surfactant is added with a medicine dropper to the diluted 6-APA solution. The solution is agitated by shaking prior to application.

Part B — Application of 6-APA Composition to Cane

A 0.3 ml dose of the aqueous solution containing 38 mg 6-APA, prepared as described in Part A above, was applied on the spindle area at the top of the last visible dewlap of each of 20 stalks of sugarcane in a test plot in a commercial cane field in Hawaii, using a syringe with a fine needle as a microapplicator.

Other groups of 20 stalks each in the same test plot were treated in an identical manner for comparative purposes (a) with Procaine Penicillin G and (b) with "Trysben" (dimethylamine salt of 2,3,6-trichlorobenzoic acid), used as a standard because of its known and consistent good activity.

The age of the cane at the time of application was 21.25 months.

As Table II shows, the ripening effect of 6-APA when applied to the crop five weeks before harvest is significantly better than that of Trysben under the same conditions.

TABLE I

| Cane Variety: | 59-3775 Field F |  |  |  |
|---|---|---|---|---|
| Age: | 21.25 months |  |  |  |
| Date of Treatment: | June 6, Year Y |  |  |  |
|  | Harvest Time After Treatment |  |  |  |
|  | 27 Days |  | 35 Days |  |
| Ripening Agent | Juice Purity | Pol % Cane | Juice Purity | Pol % Cane |
| 6-APA, 38 mg/stalk | 66.84 | 7.06 | 74.06 | 9.31 |
| Procaine Penicillin G, 38 mg/stalk | 78.12 | 9.82 | 73.89 | 8.80 |
| Trysben (standard) | 62.40 | 5.96 | 74.87 | 9.22 |
| Control (untreated) | 58.44 | 5.13 | 67.73 | 7.19 |

A set of 10 of these treated stalks from each group were harvested 27 days after such treatment and another set of 10 were harvested 35 days after such treatment. At each harvest a set of 10 untreated stalks from the same plot were also harvested as a control.

The top 15 joints of each 10-stalk set of the treated stalks, as well as those of untreated control stalks from the same test plot, were removed, and each set was combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The test data are given in Table I.

The data show that treatment with 6-APA brings about a major increase in sucrose yield as compared with the untreated cane, and that 6-APA is about as effective a ripener as the standard ripener, Trysben, or as the antibiotically active procaine penicillin G. Both 6-APA and procaine penicillin G are actually seen to be distinctly superior to Trysben in the case of cane harvested 4 weeks (27 days) after treatment, indicating that the first two compounds are unusually fast acting. Such a high rate of initial activity is of course of particular value when the cane needs to be harvested relatively soon after treatment. After another week the effect produced by 6-APA is seen to have increased and is about as good as that of Trysben, whereas the effect of procaine penicillin G is seen to have declined somewhat.

EXAMPLE 2

In this example 6-APA and Trysben, respectively, were applied to a different crop of sugarcane at a different time of year and the cane stalks were harvested five weeks later. The procedure and dosage used were the same as in Example 1. The test data are shown in Table II, below.

TABLE II

| Cane Variety: | 59-3775 Field G |  |
|---|---|---|
| Age: | 18.5 months |  |
| Date of Treatment: | December 19, Year Y |  |
| Date of Harvest: | January 22, Year Y + 1 |  |
|  | Harvest Time After Treatment |  |
|  | 5 Weeks (34 Days) |  |
| Ripening Agent | Juice Purity | Pol % Cane |
| 6-APA, 38 mg/stalk | 80.37 | 10.83 |
| Trysben (standard) | 75.45 | 9.17 |
| Control (untreated) | 69.86 | 7.18 |

EXAMPLE 3

Using the same procedure as that described above in Example 1, Part B, two different forms of penicillamine were tested in two different series of field tests as ripeners for sugarcane and compared with two different penicillins and with Trysben. The test data are shown in Tables III-A and III-B, below.

Referring to Tables III-A and III-B, it can be seen from both that the penicillamines show about the same degree of effectiveness as Trysben and as the penicillins tested when harvest follows four weeks after treatment, but the penicillamines produce a very much larger effect than Trysben when harvest follows five weeks after treatment. As shown in Table III-B, both D-penicillamine and DL-penicillamine as well as K penicillin G have a significant incremental effect during the fifth week in this test series, whereas the effect of Trysben remains more or less constant and the effect of K penicillin V actually declined during the fifth week.

As also shown in Table III-B, the effectiveness of DL-penicillamine at a dosage of 19 mg/per stalk is nearly the same as the effectiveness of the other ripeners at double this dosage.

The tabulated data show that in each test series the present invention produces a very important increase in sucrose yield over that obtained in the untreated control and in most cases a greater increase than that obtained with Trysben.

TABLE III-A

| Cane Variety: | 50-7209 | | | |
|---|---|---|---|---|
| Age: | 21 months | | | |
| Date of Treatment: | January 15, Year Y | | | |
| Dates of Harvest: | February 12 and 19, Year Y | | | |

| | Harvest Time After Treatment | | | |
|---|---|---|---|---|
| | 4 Weeks (28 Days) | | 5 Weeks (25 Days) | |
| Ripening Agent | Juice Purity | Pol % Cane | Juice Purity | Pol % Cane |
| DL-Penicillamine, 38 mg/stalk | 75.16 | 8.85 | 80.29 | 10.33 |
| K Penicillin V, 38 mg/stalk | 71.10 | 8.12 | 78.88 | 11.56 |
| Trysben (standard) | 73.05 | 9.16 | 69.40 | 8.61 |
| Control (untreated) | 66.76 | 7.34 | 66.03 | 7.15 |

TABLE III-B

| Cane Variety: | 59-3775 Field I | | | |
|---|---|---|---|---|
| Age: | 18 months | | | |
| Date of Treatment: | March 14, Year Y | | | |
| Dates of Harvest: | April 10 and 18, Year Y | | | |

| | Harvest Time After Treatment | | | |
|---|---|---|---|---|
| | 4 Weeks (27 Days) | | 5 Weeks (35 Days) | |
| Ripening Agent | Juice Purity | Pol % Cane | Juice Purity | Pol % Cane |
| D-Penicillamine, free base, 38 mg/stalk | 72.71 | 8.76 | 77.92 | 10.94 |
| DL-Penicillamine, 19 mg/stalk | 73.20 | 8.96 | 76.32 | 10.10 |
| K-Penicillin V, 38 mg/stalk | 76.62 | 9.82 | 72.91 | 8.95 |
| K Penicillin G, 38 mg/stalk | 74.62 | 9.60 | 82.83 | 12.20 |
| Trysben (standard) | 74.23 | 9.22 | 74.71 | 9.96 |
| Control (untreated) | 69.39 | 7.57 | 70.07 | 8.24 |

The data also show that ripeners used in the present invention maintain their activity fairly constant over many weeks, that 6-APA is particularly fast acting in comparison with other ripeners in the first two or three weeks after application, and that the benefits of the present invention can be obtained with similar effect at various stages of natural maturity of the cane being treated.

The nature, scope, utility and effectiveness of the present invention have been described and exemplified in the foregoing specification. However, these examples are not intended to be limiting. The true scope of the invention which is entitled to patent protection is particularly pointed out in the appended claims.

What is claimed is:

1. A process for modifying the ripening of field grown sugarcane plants so as to increase their yield of sucrose which comprises applying to the cane plants at a time from 2 to 10 weeks prior to harvest a sucrose increasing amount of a ripening agent selected from the group consisting of 6-aminopenicillanic acid, sodium, potassium and ammonium salts of 6-aminopenicillanic acid, penicillamine, and hydrochloride, sulfate and phosphate salts of penicillamine.

2. A process according to claim 1 wherein said ripening agent is sprayed onto the cane plants as a liquid composition containing water as a carrier.

3. A process according to claim 2 wherein the aqueous composition contains between 0.1 and 2% by weight of a surface active agent.

4. A process according to claim 2 wherein the aqueous composition contains between 0.1 and 2% by weight of a non-ionic surface active agent.

5. A process according to claim 1 wherein said ripening agent is 6-aminopenicillanic acid.

6. A process according to claim 1 wherein said ripening agent is D-penicillamine and is applied to the cane plants at the rate of about 1 to 4 pounds per acre.

7. A process according to claim 1 wherein said ripening agent is DL-penicillamine.

8. A process according to claim 5 wherein the 6-aminopenicillanic acid is dissolved in an aqueous composition as a sodium, potassium or ammonium salt.

9. A process according to claim 1 wherein the penicillamine is dissolved in an aqueous composition as a hydrochloride, sulfate or phosphate salt.

10. A process according to claim 1 wherein the cane plants are between 9 and 36 months of age when the ripening agent is applied thereto.

11. A process for modifying the ripening of field grown sugarcane plants so as to increase their yield of sucrose which comprises applying to the cane plants at a time from 2 to 10 weeks prior to harvest and when the plants are between 9 and 36 months of age a sucrose increasing amount in the range of from about 1 to 4 pounds per acre of a ripening agent selected from the group consisting of D-penicillamine, DL-penicillamine and the hydrochloride, sulfate and phosphate salts thereof, said ripening agent being sprayed onto the plants as an aqueous composition.

* * * * *